United States Patent
Shin et al.

(10) Patent No.: US 11,608,522 B2
(45) Date of Patent: Mar. 21, 2023

(54) METHOD OF DETECTING TARGET NUCLEIC ACID USING ROLLING CIRCLE AMPLIFICATION AND COMPOSITION FOR DETECTING TARGET NUCLEIC ACID

(71) Applicant: Korea University Research and Business Foundation, Seoul (KR)

(72) Inventors: Sehyun Shin, Seoul (KR); Won-Hwi Na, Seoul (KR); Ho Yoon Lee, Seoul (KR); Hwang-Soo Kim, Seoul (KR); Ye Eun Oh, Goyang-si (KR)

(73) Assignee: Korea University Research and Business Foundation, Seoul (KR)

( * ) Notice: Subject to any disclaimer, the term of this patent is extended or adjusted under 35 U.S.C. 154(b) by 171 days.

(21) Appl. No.: 15/733,965

(22) PCT Filed: May 31, 2019

(86) PCT No.: PCT/KR2019/006602
§ 371 (c)(1),
(2) Date: Dec. 1, 2020

(87) PCT Pub. No.: WO2019/231287
PCT Pub. Date: Dec. 5, 2019

(65) Prior Publication Data
US 2021/0155979 A1    May 27, 2021

(30) Foreign Application Priority Data

Jun. 1, 2018 (KR) .................... 10-2018-0063569
May 31, 2019 (KR) .................... 10-2019-0064750

(51) Int. Cl.
*C12Q 1/68* (2018.01)
*C12Q 1/6848* (2018.01)
*C12Q 1/686* (2018.01)

(52) U.S. Cl.
CPC ........... *C12Q 1/6848* (2013.01); *C12Q 1/686* (2013.01)

(58) Field of Classification Search
None
See application file for complete search history.

(56) References Cited

U.S. PATENT DOCUMENTS

| 9,862,994 B2 * | 1/2018 | Schmidt ............... C12Q 1/6844 |
| 10,526,641 B2 * | 1/2020 | Fields .................. C12Q 1/6806 |
| 2015/0126376 A1 | 5/2015 | Bielas et al. |

FOREIGN PATENT DOCUMENTS

| WO | WO 2004/044549 A2 | 5/2004 |
| WO | WO 2015/079042 A1 | 6/2015 |

(Continued)

OTHER PUBLICATIONS

Huang et al. (Biosensors and Bioelectronics, 2007, vol. 22, p. 980-985) (Year: 2007).*

(Continued)

*Primary Examiner* — Stephanie K Mummert
(74) *Attorney, Agent, or Firm* — NSIP Law

(57) ABSTRACT

The present invention relates to a method of detecting a target nucleic acid on the basis of rolling circle amplification (RCA), and more specifically, to a method of detecting a target nucleic acid, the method in which a target nucleic acid (a nucleic acid having a target nucleic acid sequence), when present, forms a circular template with a template for performing an amplification reaction, wherein during the amplification reaction, a restriction enzyme is added to further induce a new RCA reaction, thus increasing the reaction rate and sensitivity, and to an RCA composition for implementing the method. The method of detecting a target nucleic acid according to the present invention, by detecting a barcode sequence predefined according to the type of the target nucleic acid, enables multiple detections of the presence of the target nucleic acid without sequencing, is inexpensive for not using costly enzymes, such as CRISPR, can detect barcode sequences, and can utilize various existing nucleic acid detection systems, and thus, can be useful in the detection of gene mutations.

18 Claims, 7 Drawing Sheets

Specification includes a Sequence Listing.

(56) References Cited

FOREIGN PATENT DOCUMENTS

WO     WO 2016/016450 A1     2/2016
WO     WO 2017/177017 A1     10/2017

OTHER PUBLICATIONS

Kuhnemund et al. (NAR, 2017, 45(8):e59, p. 1-10) (Year: 2017).*
Ou, Lijuan, Aiming Sun, and Kaijian Liu. "Rolling circle amplification-based biosensors." *Analytical Letters* 48.8 (Jan. 8, 2015): pp. 1199-1216.
Extended European Search Report dated Feb. 1, 2022, in counterpart European Patent Application No. 19811578.4 (9 pages in English).
Joffroy, Bastian, et al., "Rolling circle amplification shows a sinusoidal template length-dependent amplification bias." *Nucleic acids research*, vol. 46, No. 2, Dec. 9, 2017 (pp. 538-545).
International Search Report dated Oct. 1, 2019 in counterpart International Patent Application No. PCT/KR2019/006602 (2 pages in English and 2 pages in Korean).

* cited by examiner

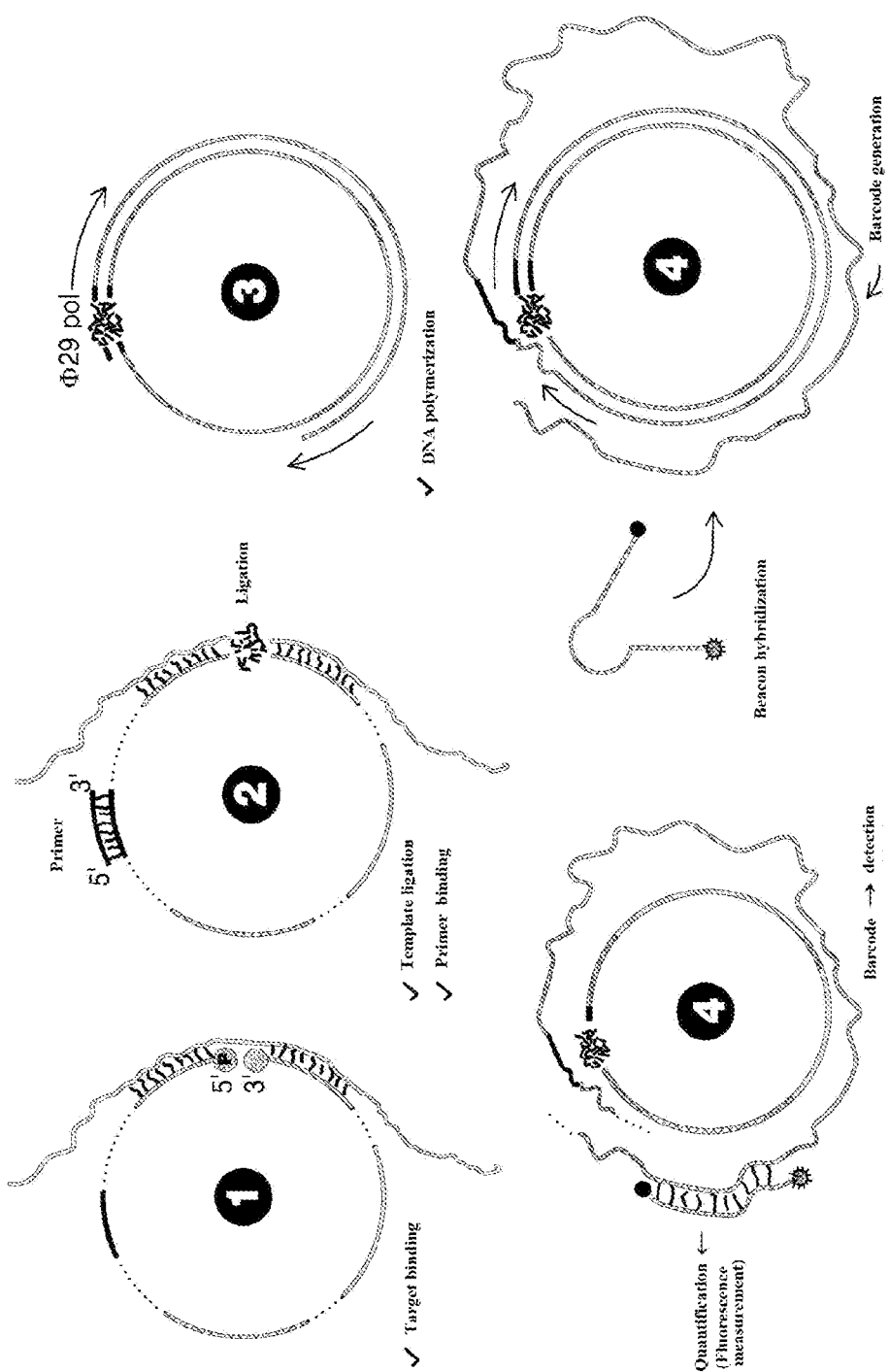
[Fig. 1]

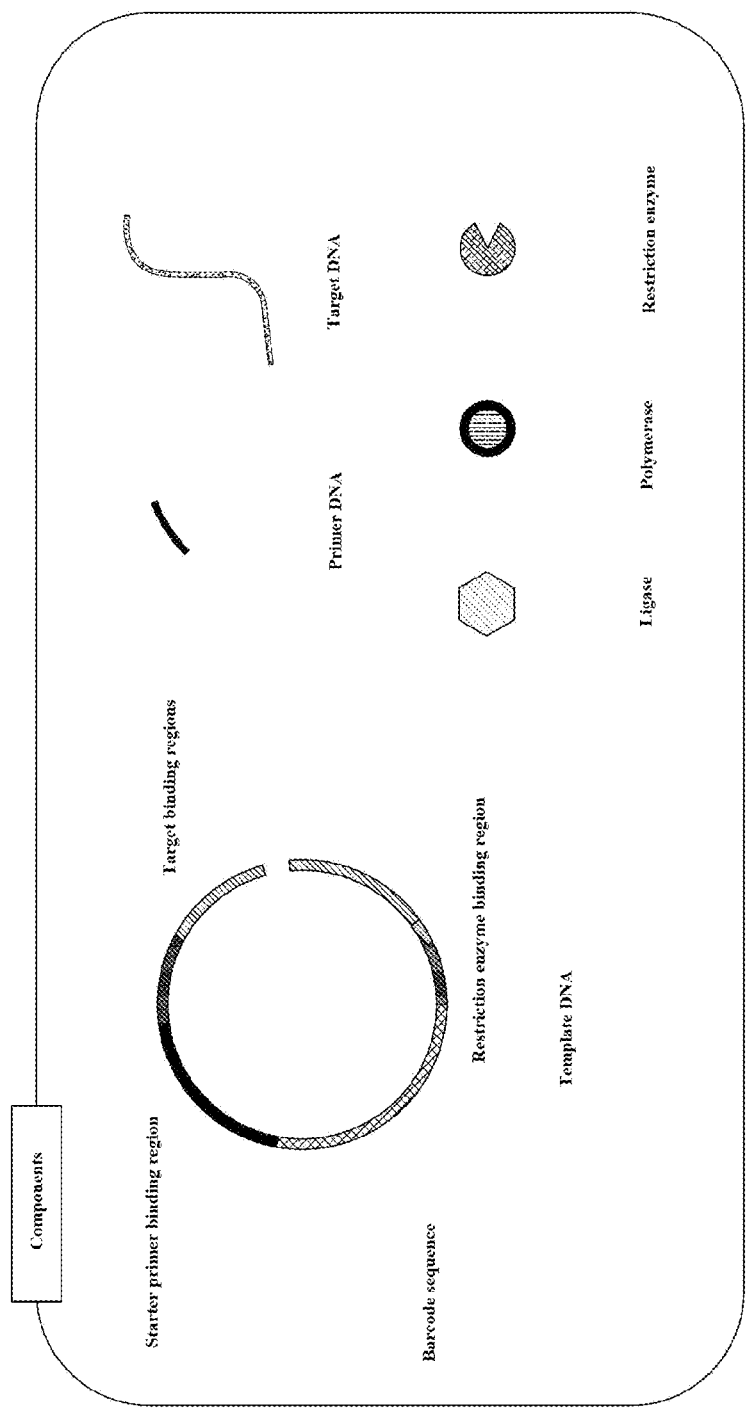
[Fig. 2]

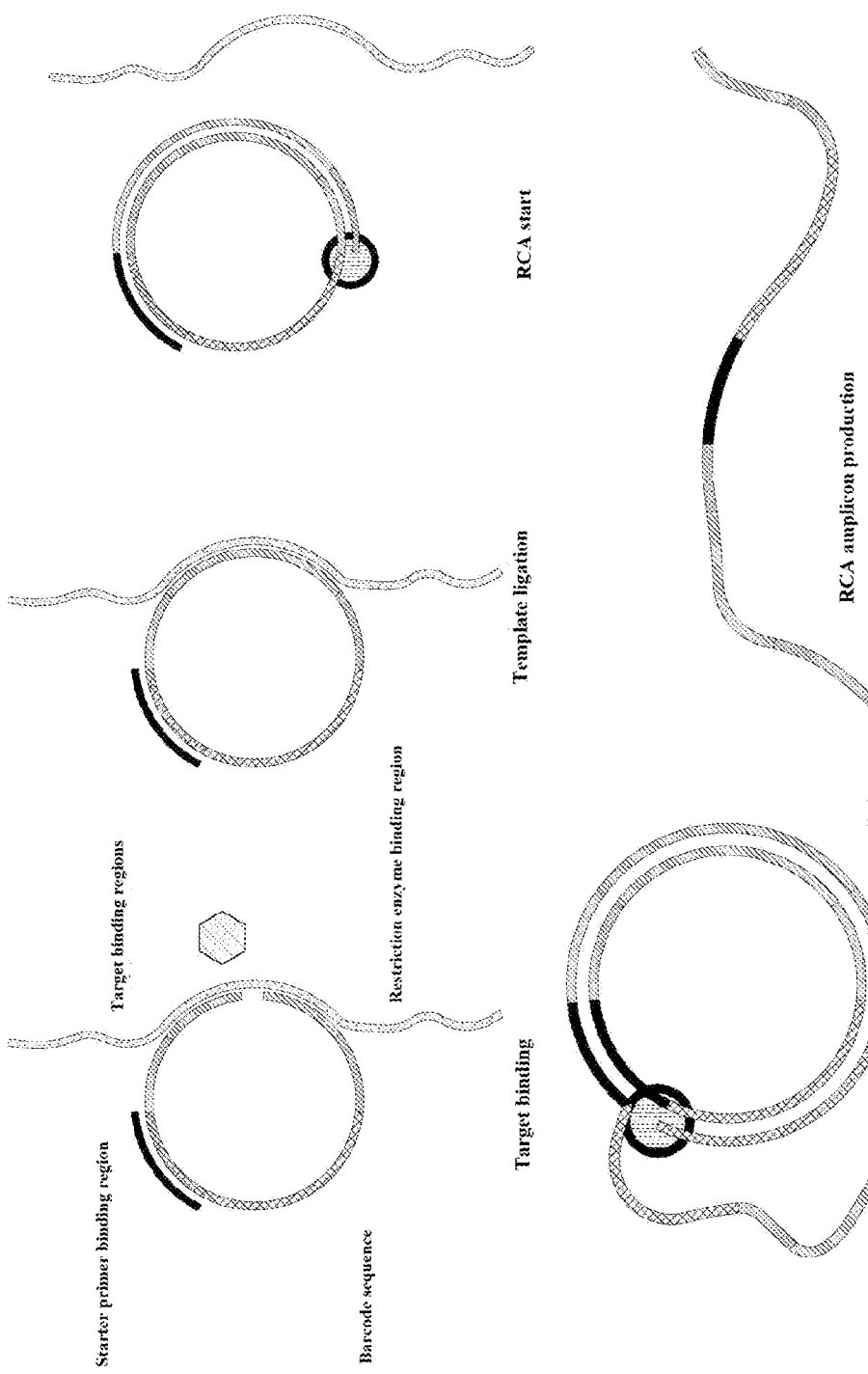
[Fig. 3]

[Fig. 4]
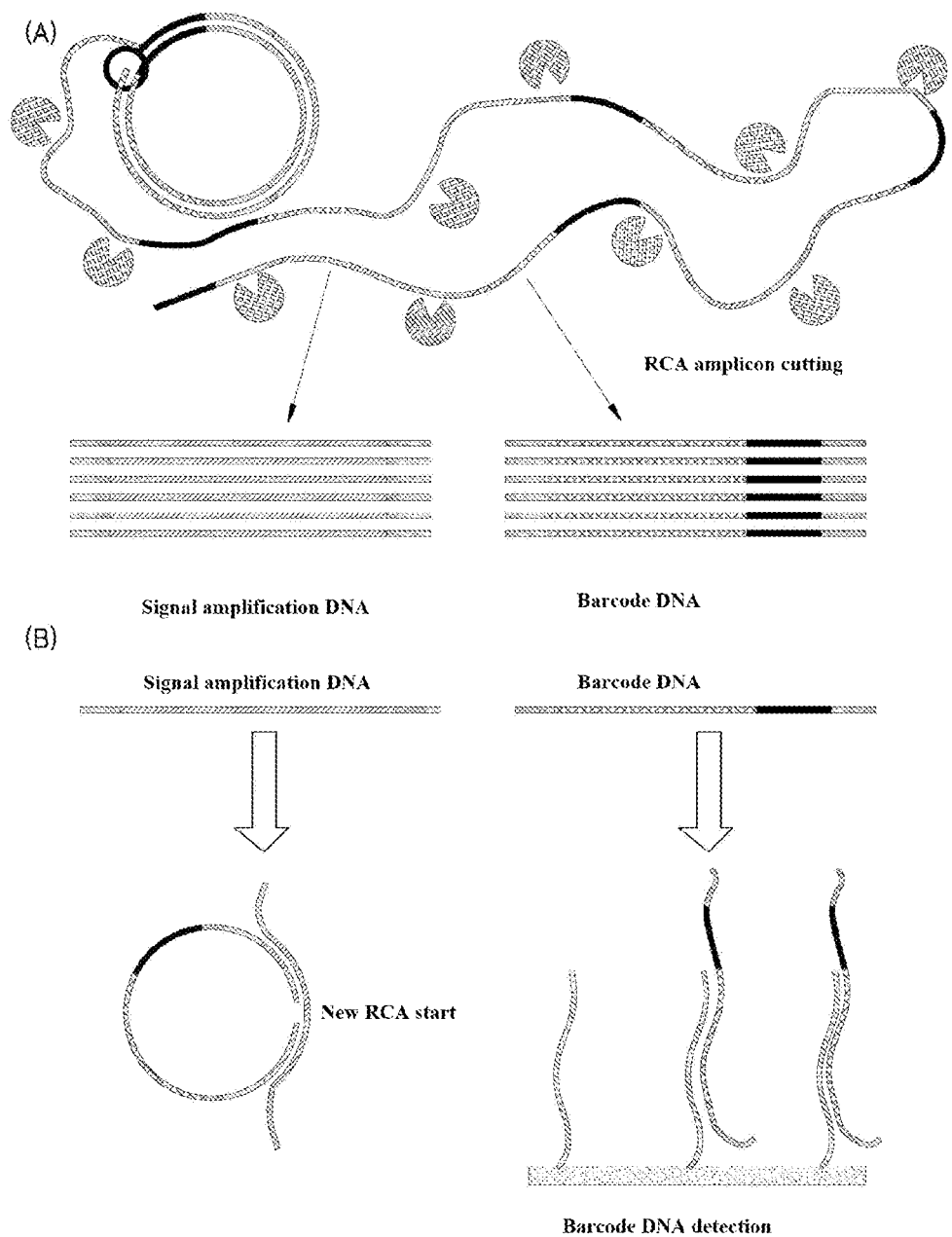

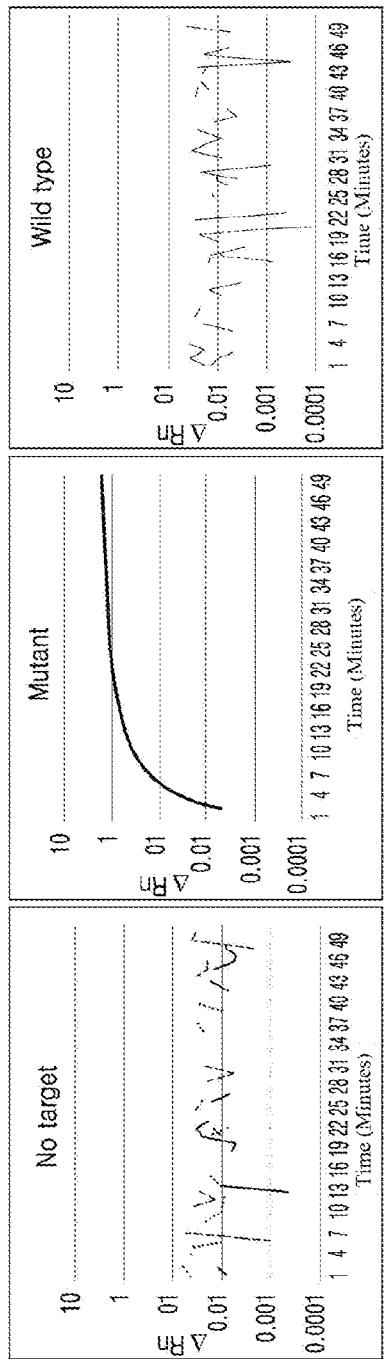
(A) Fluorescence signal detection results
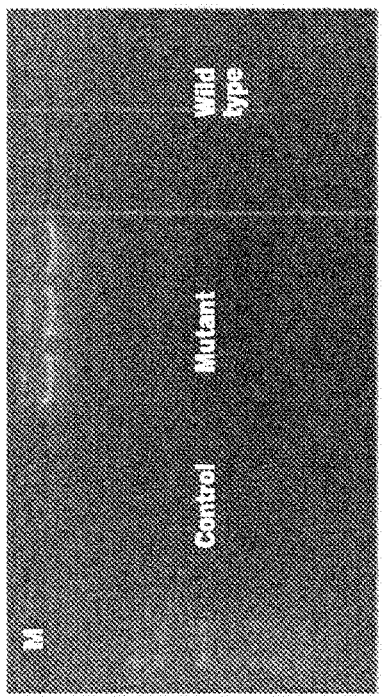
(B) Electrophoresis results
M : Marker(50bp)
[Fig. 5]

[Fig. 6]
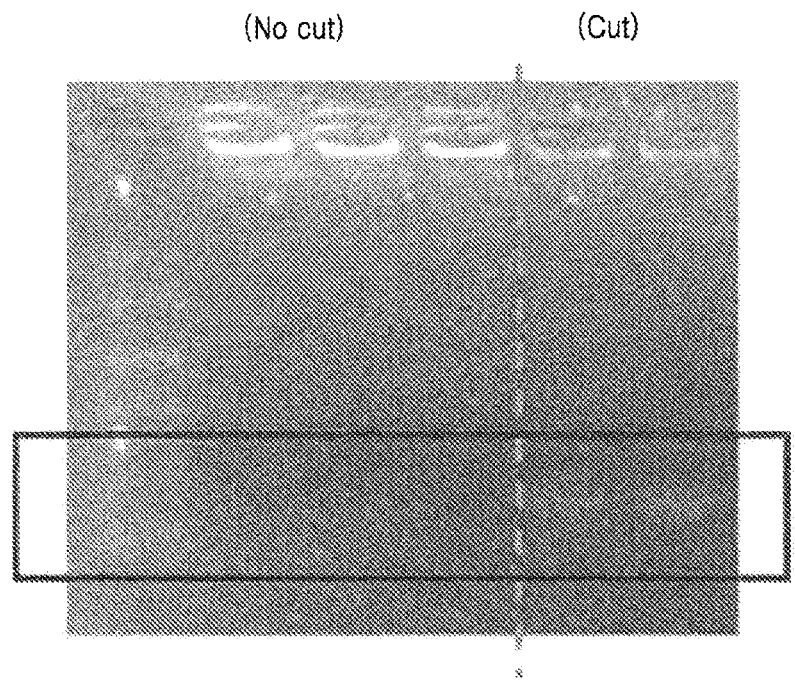
[Fig. 7]
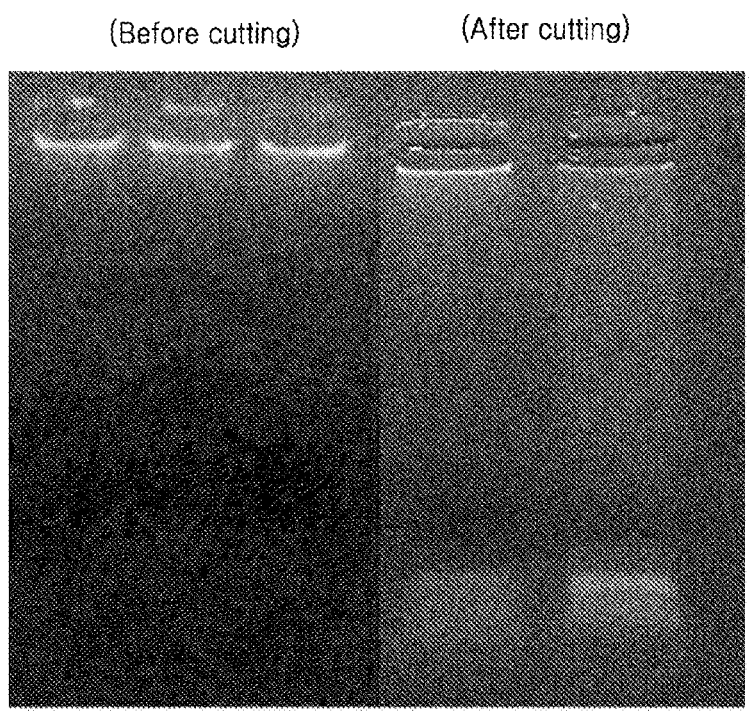

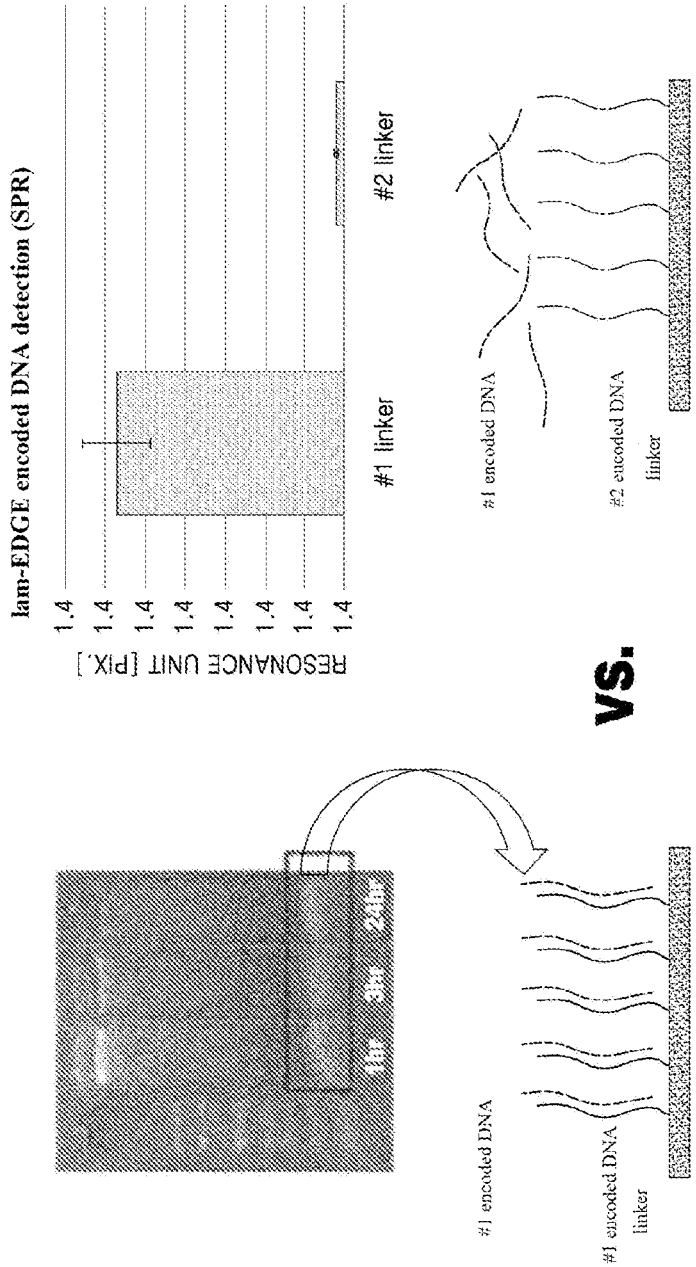
[Fig. 8]

SEQUENCE LISTING

```
<160> NUMBER OF SEQ ID NOS: 8

<210> SEQ ID NO 1
<211> LENGTH: 96
<212> TYPE: DNA
<213> ORGANISM: Artificial Sequence
<220> FEATURE:
<223> OTHER INFORMATION: Template_1

<400> SEQUENCE: 1
tagtgatttc accccgcatg ctagtatcga cgtccccaac atcagtcagc tgctgataag    60
ctgaaagcaa caaggatagg ggccccctct cctgct                              96
```

-continued

```
<210> SEQ ID NO 2
<211> LENGTH: 50
<212> TYPE: DNA
<213> ORGANISM: Artificial Sequence
<220> FEATURE:
<223> OTHER INFORMATION: Wild type

<400> SEQUENCE: 2
cgagatcctc tctctgaaat cactgagcag gagaaagatt ttctatggag          50

<210> SEQ ID NO 3
<211> LENGTH: 50
<212> TYPE: DNA
<213> ORGANISM: Artificial Sequence
<220> FEATURE:
<223> OTHER INFORMATION: Mutant

<400> SEQUENCE: 3
cgagatcctc tctctgaaat cactaagcag gagaaagatt ttctatggag          50

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
gggacgtcga tactagcatg c                                          21

<210> SEQ ID NO 5
<211> LENGTH: 38
<212> TYPE: DNA
<213> ORGANISM: Artificial Sequence
<220> FEATURE:
<223> OTHER INFORMATION: cutting DNA

<400> SEQUENCE: 5
gcgcgtcaac atcagtcagc tgctgataag ctacgcgc                        38

<210> SEQ ID NO 6
<211> LENGTH: 98
<212> TYPE: DNA
<213> ORGANISM: Artificial Sequence
<220> FEATURE:
<223> OTHER INFORMATION: Template_2

<400> SEQUENCE: 6
agtgatttca cccccatgta gtagtatcga cgtccccccc cgtataccccc ccgtttcctc    60 atatccagtt tcccccgta tacccccctc tcctgctt                              98

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
gggacgtcga tactactaca t                                          21

<210> SEQ ID NO 8
<211> LENGTH: 15
<212> TYPE: DNA
<213> ORGANISM: Artificial Sequence
```

```
<220> FEATURE:
<223> OTHER INFORMATION: cutting DNA

<400> SEQUENCE: 8
cccgtatacc ccggg                                                    15
```

METHOD OF DETECTING TARGET NUCLEIC ACID USING ROLLING CIRCLE AMPLIFICATION AND COMPOSITION FOR DETECTING TARGET NUCLEIC ACID

CROSS REFERENCE TO RELATED APPLICATIONS

This application is a U.S. National Stage Application of International Application No. PCT/KR2019/006602, filed on May 31, 2019, which claims the benefit under 35 USC 119(a) and 365(b) of Korean Patent Application No. 10-2018-0063569, filed on Jun. 1, 2018 and Korean Patent Application No. 10-2019-0064750, filed on May 31, 2019, in the Korean Intellectual Property Office, the entire disclosure of which is incorporated herein by reference for all purposes.

TECHNICAL FIELD

The present invention relates to a method for detecting a target nucleic acid based on rolling circle amplification. More specifically, the present invention relates to a method for detecting a target nucleic acid in which a target nucleic acid, if present, forms a circular template with a template, the circular template is used for amplification, and a restriction enzyme is added during amplification to further induce new RCA, achieving high reaction rate and increased sensitivity, and a composition for rolling circle amplification (RCA) for carrying out the method.

BACKGROUND ART

In current nucleic acid-based cancer diagnostics, the greatest difficulties are encountered in detecting genetic mutations in the form of point mutations. Various technologies such as next generation sequencing (NGS) and droplet digital PCR (ddPCR) are used to detect point mutations. NGS is advantageous in massively identifying many regions at one time but suffers from difficulty in distinguishing errors and real data in the detection of low-frequency point mutation genes (Buck M J et al., Cancer Prev Res (Phila). 2012, Vol. 5(7) pp. 887-900). Thus, when a point mutation is present at a specific point, it is necessary to construct a primer and a probe adapted to the corresponding portion and reconfirm the corresponding portion by ddPCR. Further, NGS is limited in that several days are required for examination and considerable costs are incurred for analysis. ddPCR enables the identification of only one mutation in one reagent tube because it has difficulty in multiplexed detection, unlike NGS. Accordingly, ddPCR has a limitation in that many reagents are consumed to completely examine a large number of major point mutation genes, incurring high costs.

General detection methods using DNA complementary binding fail to distinguish between normal genes and mutation genes and often recognize different genes as the same signal due to their difficulty in distinguishing minute differences such as point mutations.

In attempts to overcome the above limitations, methods for detecting point mutation genes using suitable enzymes such as CRISPR cas9 have been developed or are currently being developed (Zhang F et al., Science. 2017. Vol. 28; 356(6336). pp. 438-442). CRISPR cas9 is a technique for detecting specific mutation genes without the above system due to its enzymatic activity. However, CRISPR cas9 has the greatest limitation that only limited mutation sequences can be recognized and is unsuitable for diagnostic purposes due to its very high price. CRISPR is used in combination with RNA fragments but this combination can be used only in laboratory experiments due to the instability of RNA.

The present inventors have earnestly and intensively conducted research to develop a method for simultaneously detecting various types of target nucleic acids, and as a result, found that various types of target nucleic acids can be simultaneously detected with high sensitivity and accuracy by using a linear template including i) target nucleic acid binding regions arranged at both ends to complementarily bind to a target nucleic acid sequence, ii) a primer binding region, iii) a restriction enzyme binding region, and iv) a barcode generation region in combination with a restriction enzyme upon rolling circle amplification to produce amplicons of a predefined barcode region depending on the presence or absence of a target nucleic acid including the target nucleic acid sequence and detecting the amplicons. The present invention has been accomplished based on this finding.

The information described in the Background Art section is merely provided for better understanding the background of the invention and may not contain information on the prior art already known to those having ordinary skill in the art to which the invention pertains.

DETAILED DESCRIPTION OF THE INVENTION

Problems to be Solved by the Invention

One object of the present invention is to provide a method for detecting a target nucleic acid with high sensitivity.

A further object of the present invention is to provide a composition for detecting a target nucleic acid with high sensitivity based on rolling circle amplification.

Means for Solving the Problems

The present invention provides a method for detecting a target nucleic acid based on rolling circle amplification (RCA), including (a) preparing a single-stranded nucleic acid from a sample, (b) binding a linear template including i) target nucleic acid binding regions arranged at both ends to complementarily bind to a target nucleic acid sequence, ii) a primer binding region, iii) a restriction enzyme binding region, and iv) a barcode generation region to the single-stranded nucleic acid, followed by ligation to form a circular template-target nucleic acid complex, (c) performing rolling circle amplification in the presence of a primer binding to the primer binding region and a cleavable nucleic acid having the same sequence as that of the restriction enzyme binding region to produce a single-stranded amplicon and treating the single-stranded amplicon with a restriction enzyme such that regions where the single-stranded amplicon complementarily binds to the cleavable nucleic acid are cut to obtain first amplicons including barcodes having a sequence complementary to the barcode generation region and second amplicons including the target nucleic acid sequence, and (d) detecting the barcodes of the first amplicons to determine whether or not the target nucleic acid sequence is present, wherein the circular template-target nucleic acid complex is formed and the barcodes are generated when the target nucleic acid sequence is present in the single-stranded nucleic acid.

The present invention also provides a composition for detecting a target nucleic acid based on rolling circle amplification, including (a) a linear template including i) target nucleic acid binding regions arranged at both ends to complementarily bind to a target nucleic acid sequence, ii) a primer binding region, iii) a restriction enzyme binding region, and iv) a barcode generation region, (b) a primer binding to the primer binding region, (c) a cleavable nucleic acid having the same sequence as that of the restriction enzyme binding region, (d) a restriction enzyme, and (e) a ligase.

Effects of the Invention

The method of the present invention can be used to detect a predefined barcode sequence depending on the type of a target nucleic acid so that the presence of multiple target nucleic acids can be detected simultaneously without sequencing. In addition, the method of the present invention is economically advantageous because it avoids the need to use expensive enzymes such as CRISPR. Furthermore, the method of the present invention can use various an existing nucleic acid detection system for barcode sequence detection. Therefore, the method of the present invention is useful for genetic mutation detection. The composition of the present invention can be used to detect a target nucleic acid based on RCA. The composition of the present invention uses a template adapted to a target nucleic acid so that multiple targets can be detected simultaneously in one reaction and mutations at a base level can be detected with high sensitivity. Therefore, the composition of the present invention is useful for various molecular diagnostics.

BRIEF DESCRIPTION OF THE DRAWINGS

FIG. 1 shows a method for elucidating the mechanism of barcode sequence generation in the presence of a target nucleic acid sequence by fluorescence detection in the present invention.

FIG. 2 schematically shows the structures of enzymes and DNAs required for a method of the present invention.

FIG. 3 is a simulation diagram showing the steps of rolling circle amplification in a method of the present invention.

FIG. 4 is (A) a simulation diagram showing products obtained by the activity of a restriction enzyme during RCA in a method of the present invention and (B) a simulation diagram showing the roles of the products.

FIG. 5 shows (A) the detection results of wild-type and mutant PIK3CA E545K by fluorescence signal detection in accordance with one embodiment of the present invention and (B) the results of electrophoresis for wild-type and mutant PIK3CA E545K.

FIG. 6 shows the results of electrophoresis for RCA amplicons of the wild-type and mutant PIK3CA genes after treatment with a restriction enzyme in accordance with one embodiment of the present invention (Example 1).

FIG. 7 shows the results of electrophoresis for RCA amplicons of the wild-type and mutant PIK3CA genes after treatment with a restriction enzyme in accordance with one embodiment of the present invention (Example 2).

FIG. 8 shows the detection results of barcoded amplicons using a surface plasmon resonance sensor in accordance with one embodiment of the present invention.

BEST MODE FOR CARRYING OUT THE INVENTION

Unless otherwise defined, all technical and scientific terms used herein have the same meaning as commonly understood by one of ordinary skill in the art to which this invention belongs. In general, the nomenclature used herein is well known and commonly employed in the art.

In the present invention, a specially designed template is used in the presence of a restriction enzyme during rolling circle amplification to determine whether a target nucleic acid can be detected.

Specifically, in one embodiment of the present invention, a template including i) target nucleic acid binding regions arranged at both ends to complementarily bind to a target nucleic acid sequence, ii) a primer binding region, iii) a restriction enzyme binding region, and iv) a barcode generation region is allowed to bind to a single-stranded target nucleic acid, followed by ligation to construct a circular template, rolling circle amplification is performed, the resulting amplified barcode region is treated with a restriction enzyme during rolling circle amplification to obtain separate barcode regions, and the separate barcode regions are detected. As a result, various types of target nucleic acids can be simultaneously detected (FIGS. 1 to 4).

In one aspect, the present invention is directed to a method for detecting a target nucleic acid based on rolling circle amplification (RCA), including (a) preparing a single-stranded nucleic acid from a sample, (b) binding a linear template including i) target nucleic acid binding regions arranged at both ends to complementarily bind to a target nucleic acid sequence, ii) a primer binding region, iii) a restriction enzyme binding region, and iv) a barcode generation region to the single-stranded nucleic acid, followed by ligation to form a circular template-target nucleic acid complex, (c) performing rolling circle amplification in the presence of a primer binding to the primer binding region and a cleavable nucleic acid having the same sequence as that of the restriction enzyme binding region to produce a single-stranded amplicon and treating the single-stranded amplicon with a restriction enzyme such that regions where the single-stranded amplicon complementarily binds to the cleavable nucleic acid are cut to obtain first amplicons including barcodes having a sequence complementary to the barcode generation region and second amplicons including the target nucleic acid sequence, and (d) detecting the barcodes of the first amplicons to determine whether or not the target nucleic acid sequence is present, wherein the circular template-target nucleic acid complex is formed and the barcodes are generated when the target nucleic acid sequence is present in the single-stranded nucleic acid.

As used herein, the term "target nucleic acid" is intended to mean all types of nucleic acids to be detected. This term is intended to include not only gene sequences derived from different species, subspecies, and variants, but also gene mutations in the same species. The target nucleic acid may be selected from, but not limited to, all types of DNAs, including genomic, mitochondrial, and viral DNAs, and all types of RNAs, including messenger, ribosomal, non-coding, transfer, and viral RNAs.

The target nucleic acid may be a nucleic acid including a mutation sequence but is not limited thereto. The mutation is selected from the group consisting of, but not limited to, single nucleotide polymorphism (SNP), insertion, deletion, point mutation, fusion mutation, translocation, inversion, and loss of heterozygosity (LOH).

As used herein, the term "nucleoside" refers to a glycosylamine compound in which a nucleic acid base (nucleobase) is linked to a sugar moiety. As used herein, the term "nucleotide" refers to a nucleoside phosphate. Nucleotides may be represented using alphabetical letters (letter designation), as shown in Table 1. For example, A denotes adenosine (a nucleoside containing the nucleobase, adenine), C denotes cytidine, G denotes guanosine, U denotes uridine, and T denotes thymidine (5-methyluridine). W denotes either A or T/U, and S denotes either G or C. N represents a random nucleoside and dNTP represents deoxyribonucleoside triphosphate. N may be any of A, C, G, or T/U.

TABLE 1

| Symbol letter | Nucleotide represented by the symbol letter |
|---|---|
| G | G |
| A | A |
| T | T |
| C | C |
| U | U |
| R | G or A |
| Y | T/U or C |
| M | A or C |
| K | G or T/U |
| S | G or C |
| W | A or T/U |
| H | A or C or T/U |
| B | G or T/U or C |
| V | G or C or A |
| D | G or A or T/U |
| N | G or A or T/U or C |

As used herein, the term "oligonucleotide" refers to an oligomer of nucleotides. As used herein, the term "nucleic acid" refers to a polymer of nucleotides. As used herein, the term "sequence" refers to a nucleotide sequence of an oligonucleotide or a nucleic acid. Throughout the specification, whenever an oligonucleotide or nucleic acid is represented by a sequence of letters, the nucleotides are in 5'→3' order from left to right. The oligonucleotides or nucleic acids may be DNAs, RNAs or their analogues (for example, phosphorothioate analogues). The oligonucleotides or nucleic acids may also include modified bases and/or backbones (for example, modified phosphate linkage or modified sugar moiety). Non-limiting examples of synthetic backbones that confer stability and/or other advantages to the nucleic acids may include phosphorothioate linkages, peptide nucleic acids, locked nucleic acids, xylose nucleic acids, and analogues thereof.

As used herein, the term "nucleic acid" refers to a nucleotide polymer and includes known analogs of natural nucleotides that can function (e.g., hybridize) in a similar manner to naturally occurring nucleotides, unless otherwise limited.

The term "nucleic acid" is intended to include any form of DNA or RNA, including, for example, genomic DNA; complementary DNA (cDNA), which is a DNA representation of mRNA, usually obtained by reverse transcription of messenger RNA (mRNA) or by amplification; DNA molecules produced synthetically or by amplification; and mRNA.

The term "nucleic acid" encompasses double- or triple-stranded nucleic acids, as well as single-stranded molecules. In double- or triple-stranded nucleic acids, the nucleic acid strands need not be coextensive (i.e, a double-stranded nucleic acid need not be double-stranded along the entire length of both strands).

The term "nucleic acid" also encompasses any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications may include base modifications such as 2'-position sugar modifications, 5-position pyrimidine modifications, 8-position purine modifications, modifications at cytosine exocyclic amines, substitutions of 5-bromo-uracil, backbone modifications, unusual base pairing combinations such as the isobases isocytidine and isoguanidine, and the like.

The nucleic acids can be derived from a completely chemical synthesis process, such as a solid phase-mediated chemical synthesis, from a biological source, such as through isolation from any species that produces nucleic acid, or from processes that involve the manipulation of nucleic acids by molecular biology tools, such as DNA replication, PCR amplification, reverse transcription, or from a combination of those processes.

As used herein, the term "complementary" refers to the capacity for precise pairing between two nucleotides. That is, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. The degree of complementarity between nucleic acid strands has significant effects on the efficiency and strength of hybridization between nucleic acid strands.

As used herein, the term "primer" refers to a short linear oligonucleotide that hybridizes to a target nucleic acid sequence (e.g., a DNA template to be amplified) to prime a nucleic acid synthesis reaction. The primer may be an RNA oligonucleotide, a DNA oligonucleotide, or a chimeric sequence. The primer may contain natural, synthetic, or modified nucleotides. Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3 nucleotides long) do not form thermodynamically stable duplexes with target nucleic acid under such hybridization conditions. The upper limit is often determined by the possibility of having a duplex formation in a region other than the pre-determined nucleic acid sequence in the target nucleic acid. Generally, suitable primer lengths are in the range of about 3 to about 40 nucleotides long.

As used herein, the term "rolling circle amplification (RCA)" refers to a nucleic acid amplification reaction that amplifies a circular nucleic acid template (e.g., single stranded DNA circles) via a rolling circle mechanism. Rolling circle amplification reaction may be initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). Rolling circle amplification typically produces concatamers comprising tandem repeat units of the circular nucleic acid template sequence. The rolling circle amplification may be a linear RCA (LRCA) exhibiting linear amplification kinetics (e.g., RCA using a single specific primer) or may be an exponential RCA (ERCA) exhibiting exponential amplification kinetics. Rolling circle amplification may also be performed using multiple primers (multiply primed rolling circle amplification or MPRCA) leading to hyper-branched concatamers. For example, in a double-primed RCA, one primer may be complementary, as in the LRCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This often generates a discrete set of concatemeric, double-stranded nucleic acid amplification products. Rolling circle amplification may be performed in vitro under isothermal conditions using a suitable nucleic acid polymerase such as Phi29 DNA polymerase.

As used herein, the term "probe" is a nucleic acid capable of binding to a target nucleic acid of complementary sequence through one or more types of chemical bonds, generally through complementary base pairing, usually through hydrogen bond formation, thus forming a duplex structure. The probe binds or hybridizes to a "probe binding region." The probe can be labeled with a detectable label to permit facile detection of the probe, particularly once the probe has hybridized to its complementary target. Alternatively, however, the probe may be unlabeled, but may be detectable by specific binding with a ligand that is labeled, either directly or indirectly. Probes can vary significantly in size. Generally, probes are at least 7 to 15 nucleotides in length. Other probes are at least 20, 30, or 40 nucleotides long. Still other probes are somewhat longer, being at least 50, 60, 70, 80, or 90 nucleotides long. Yet other probes are longer still and are at least 100, 150, 200 or more nucleotides long. Probes can also be of any length that is within any range bounded by any of the above values (e.g., 15-20 nucleotides in length).

As used herein, the term "hybridization" means the formation of a double-stranded nucleic acid by hydrogen bonding between single-stranded nucleic acids having complementary sequences. This term is used to have a meaning similar to annealing. In a broader sense, hybridization includes not only a perfect match where two single strands have completely complementary sequences but also a mismatch where the sequences of two single strands are complementary except at some base positions.

In the present invention, the template is a single-stranded linear nucleic acid.

In the present invention, the target nucleic acid binding regions of the template are present at both ends of the template.

In the present invention, the barcodes have a predefined sequence depending on the target nucleic acid and do not complementarily bind to the target nucleic acid.

In the present invention, each of the second amplicons is provided as a single-stranded nucleic acid in step (a). That is, each of the second amplicons obtained in step (c) acts as a single-stranded nucleic acid including the target nucleic acid sequence, and thereafter, steps (b) to (d) are repeated such that the target nucleic acid sequence-containing DNA cut in step (c) binds to a new template DNA and new RCA is performed. According to the present invention, second amplicons including the target nucleic acid sequence and first amplicons including the barcode region are produced by the activity of a restriction enzyme rather than one long amplicon is produced by rolling circle amplification, and the amplicons including the target nucleic acid cut by the restriction enzyme bind to another template to induce new rolling circle amplification, resulting in improved sensitivity as well as signal amplification.

In the present invention, the target nucleic acid is present in plurality. In this case, barcode generation regions of different templates corresponding to the target nucleic acids are amplified to generate barcodes and the target nucleic acids are detected using the barcodes.

For example, when the target nucleic acids are a point mutation of PIK3CA, a point mutation of EGFR, a point mutation of p53, and a point mutation of BRCA1/2, different barcode generation regions corresponding to the target point mutations may be designed for simultaneous detection.

In the present invention, the target nucleic acid binding regions of the template are designed such that a point of interest of the target nucleic acid is ligated to the template by a ligase. The method of the present invention can be used to detect a point mutation in which the glutamic acid residue at position 545 in the PIK3CA protein is converted to lysine, that is, the base G at position 1633 in the PIK3CA gene is mutated to base A. In this case, the $10^{th}$ to $20^{th}$ bases in the 5' upstream direction from the base at position 1633 bind to the first target nucleic acid binding region and the $10^{th}$ to $20^{th}$ bases in the 3' downstream direction from the base at position 1633 bind to the second target nucleic acid binding region, followed by ligation to form a circular template-target nucleic acid complex.

In step (a), the single-stranded nucleic acid may be prepared by any known method for preparing a single-stranded nucleic acid from a nucleic acid extracted from a sample. The single-stranded nucleic acid is preferably prepared by asymmetric polymerase chain reaction (PCR) but the present invention is not limited thereto.

In step (a), the single-stranded nucleic acid may be prepared by denaturing double-stranded deoxyribonucleic acid (DNA) extracted from a sample and complementarily binding a blocker DNA to only one single strand of the denatured double-stranded deoxyribonucleic acid.

The barcodes of the first amplicons produced by amplification of the barcode generation region in step (c) are detected using a surface measurement sensor including a probe complementary to the barcodes but the present invention is not limited thereto. It will be evident to those skilled in the art that the sequence of the probe complementary to the barcodes is the same as that of the barcode generation region of the template.

In the present invention, the surface measurement sensor may operate based on a method selected from the group consisting of, but not limited to, fluorescence, surface plasmon resonance (SPR), quartz crystal microbalance (QCM), and cantilevers.

In the present invention, the probe complementary to the barcode region is selected from the group consisting of, but not limited to, oligonucleotides, locked nucleic acids (LNAs), peptide nucleic acids (PNAs), and mixtures thereof.

Peptide nucleic acids (PNAs) are DNA mimics in which nucleic acid bases are linked to a peptide backbone rather than the sugar-phosphate backbone. The first PNA was synthesized by Nielsen, et al. in 1991. PNAs are substances that can recognize genes, like locked nucleic acids (LNAs) or morpholino nucleic acids (MNAs). They are artificially synthesized and have a backbone consisting of polyamide.

PNAs are excellent in affinity and selectivity and are not degraded by existing restriction enzymes due to their high stability against nucleases. In addition, PNAs are easy to store due to their excellent thermal/chemical properties and high stability.

PNA forms a double strand by hybridization with a natural nucleic acid having a sequence complementary thereto. PNA/DNA double strands are more stable than DNA/DNA double strands having the same length and PNA/RNA double strands are more stable than DNA/RNA double strands having the same length. The ability of PNA to detect single nucleotide polymorphism (SNP) is better than that of natural nucleic acids because a single base mismatch causes more destabilization of PNA double strands.

In the present invention, the surface measurement sensor may operate based on fluorescence. In this case, a report and a quencher are linked to both ends of the probe complementary to the barcodes.

In the present invention, the generation of signals from the probe is suppressed when the reporter is close to the quencher whereas the intensity of signals from the probe increases with increasing distance between the reporter and the quencher. Generally, hybridization of the probe with a complementary sequence makes the reporter and the quencher most distant from each other, enabling detection of the specific sequence through the generation of signals or the increased signal intensity.

In the present invention, the reporter may be at least one fluorescent material selected from the group consisting of, but not limited to, fluorescein, fluorescein chlorotriazinyl, rhodamine green, rhodamine red, tetramethylrhodamine, FITC, Oregon green, Alexa Fluor, FAM, JOE, ROX, HEX, Texas Red, TET, TRITC, TAMRA, cyanine-based dyes, and thiadicarbocyanine dyes.

In the present invention, the quencher may be selected from the group consisting of Dabcyl, TAMRA, Eclipse, DDQ, QSY, Blackberry Quencher, Black Hole Quencher, Qxl, Iowa black FQ, Iowa black RQ, IRDye QC-1, and mixtures thereof.

In step (b), the ligation may be performed using T7 DNA ligase, but the present invention is not limited thereto.

In step (c), the rolling circle amplification may be performed using phi29 DNA polymerase for DNA polymerization, but the present invention is not limited thereto.

In the present invention, the template may further include a spacer region and a fluorescent probe binding region.

In the present invention, the restriction enzyme binding region of the template may be present in plurality.

In the present invention, the cleavable nucleic acid may further include sequences at the 5' and 3' ends thereof which do not bind to the template. In the present invention, since the sequence of the restriction enzyme binding region of the single-stranded amplicon produced by RCA is complementary to that of the restriction enzyme binding region of the template, the cleavable nucleic acid having the same sequence as that of the restriction enzyme binding region of the template binds to the restriction enzyme binding region of the single-stranded amplicon produced by RCA to form a double strand. The double strand is cut into strands by the restriction enzyme. The additional 5' and 3' terminal sequences which do not bind to the template prevent the strands from acting as primers to induce further polymerization.

In the present invention, the cleavable nucleic acid may further include functional groups or bases at the 5' and 3' ends thereof which inhibit nucleic acid polymerization.

In the present invention, the additional 5' and 3' terminal functional groups or bases may be selected from the group consisting of, but not limited to, amine groups, phosphate groups, alkyl groups, alkane-diols, phosphorothioates, biotin, non-nucleotide linkers, C3-18 spacers, dideoxynucleotide triphosphates (ddNTPs), inverted deoxynucleotide triphosphates (inverted dNTPs), inverted dideoxynucleotide triphosphates (inverted ddNTP), and mixtures thereof.

In a further aspect, the present invention is directed to a composition for detecting a target nucleic acid based on rolling circle amplification, including (a) a linear template including i) target nucleic acid binding regions arranged at both ends to complementarily bind to a target nucleic acid sequence, ii) a primer binding region, iii) a restriction enzyme binding region, and iv) a barcode generation region, (b) a primer binding to the primer binding region, (c) a cleavable nucleic acid having the same sequence as that of the restriction enzyme binding region, (d) a restriction enzyme, and (e) a ligase.

As used herein, the term "sample" is meant to include various kinds of samples. Preferably, a biological sample is analyzed by the method of the present invention. More preferably, the sample contains a viral species or is a sample from individuals (for example, humans, mammals, and fish) infected with the virus. Biological samples originating from plants, animals, humans, fungi, bacteria, and viruses can be analyzed by the present invention. The sample may originate from a specific tissue or organ of a mammal or human Representative examples of such tissues include connective, epithelial, muscular, and nervous tissues. Representative examples of such organs include eye, brain, lung, liver, spleen, bone marrow, thymus, heart, lymph, blood, bone, cartilage, pancreas, kidney, gall bladder, stomach, small intestine, testis, ovary, uterus, rectum, nervous system, gland, and internal blood vessel. The biological sample contains any cell, tissue or fluid from a biological source or any other medium that can be well analyzed by the present invention. The biological sample may be obtained from foods that are produced for consumption by humans and/or animals. The biological sample may be a bodily fluid sample. Examples of such bodily fluids include, but are not limited to, blood, serum, plasma, lymph, breast milk, urine, feces, ocular fluid, saliva, semen, brain extracts (e.g., brain homogenates), spinal fluid, appendix, spleen, and tonsillar tissue extracts.

In another aspect, the present invention is directed to a kit for detecting a target nucleic acid including the composition.

In the present invention, the kit of the present invention may optionally include at least one reagent required for amplification of a target nucleic acid (e.g., polymerase chain reaction). Examples of such reagents include buffers, DNA polymerases, DNA polymerase cofactors, and deoxyribonucleotide-5-triphosphates (dNTPs). The kit of the present invention may optionally include oligonucleotide molecules, reverse transcriptases, buffers, reagents, and antibodies capable of inhibiting the activity of DNA polymerases. The optimal amount of the reagent used for the specific reaction in the kit can be easily determined by those skilled in the art who have understood the disclosure set forth herein. Typically, the system of the present invention contains the above-mentioned components in separate packages or compartments.

In one embodiment, the kit may include carrier means divided to accommodate a sample, a container accommodating the reagents, a container accommodating a substitution target and the primer, and a container accommodating a probe for detecting the amplicons.

The carrier means is adapted to accommodate one or more containers such as bottles and tubes, each of which independently contains the elements used in the method of the present invention. Herein, those skilled in the art can readily dispense necessary agents in the containers.

MODE FOR CARRYING OUT THE INVENTION

The present invention will be explained in more detail with reference to the following examples. It will be evident to those skilled in the art that these examples are merely for illustrative purposes and are not to be construed as limiting the scope of the present invention.

Example 1. Confirmation of Efficacy of the RCA-Based Method for Detecting Target Nucleic Acid

1.1. Construction of Template, Primer and Beacon 50 bases around the E545K point mutation of the PIK3CA gene were selected as a target gene and a template, a primer, and a beacon for amplicon detection were constructed, as shown in Table 2, to determine whether the E545K point mutation could be detected by the inventive method.

TABLE 2

Nucleic acid sequences generated in Example 1

| SEQ ID NO. | Name | Sequence |
|---|---|---|
| 1 | Template | 5'-T ACT GAT TTC A(1) CCC C(2)GC ATG CTA GTA TCG ACG TCC C(3) CAA CAT CAG TCA GCT GCT GAT AAG CT(4) GAA AGC AAC AAG GAT AGG GG (5) CC CCC(6) T CTC CTG CT(7)-3' |
| 2 | Wild type | 5'-CGA GAT CCT CTC TCT GAA ATC ACT GAG CAG GAG AAA GAT TTT CTA TGG AG-3' |
| 3 | Mutant | 5'-CGA GAT CCT CTC TCT GAA ATC ACT AAG CAG GAG AAA GAT TTT CTA TGG AG-3' |
| 4 | primer | 5'-G GGA CGT CGA TAC TAG CAT GC-3' |
| 5 | Cleavable DNA | 5'-FAM-GCG CGT CAA CAT CAG TCA GCT GCT GAT AAG CTA CGC GC-Dabcyl-3' |

The sequence of the template is as follows.

5' phosphate-(1): First target binding region in which the first base T complementarily binds to the base A shown in bold in the sequence (SEQ ID NO: 3) of the mutant.

- (1)-(2): Spacer
- (2)-(3): Primer binding region
- (3)-(4): Fluorescent probe binding region
- (4)-(5): Barcode generation region
- (5)-(6): Spacer
- (6)-(7): Second target binding region

1.2. Discrimination of Mutant/Wild Type by RCA

The target nucleic acid having the sequence set forth in SEQ ID NO: 2 or 3 and the primer having the sequence set forth in SEQ ID NO: 4 were introduced into the template constructed in Example 1.1. Then, RCA was performed using the components in the amounts shown in Table 3. The results were evaluated by electrophoresis and fluorescence signal detection using the beacon.

As a result, RCA proceeded only for the mutant to produce a very long RCA amplicon and generate fluorescence signals, as shown in FIG. 5.

TABLE 3

| E545K New RCA | | | |
|---|---|---|---|
| Component | Con | Vol | (Each Component *1.1 *9) |
| 4 µM Template _ E545K | 4 | 2.5 | 24.75 |
| 100 µM target(MU/WT) | 100 | 1.25 | Respectively |
| Phi 29 polymerase butter | 10 | 5 | 49.50 |
| 100 mM DTT | 100 | 1.25 | 12.38 |
| 25 mM dNTP | 25 | 5 | 49.50 |
| 50 mM ATP | 50 | 1.25 | 12.38 |
| 10 mg/ml BSA | 10 | 1.25 | 12.38 |
| 10 µM starting primer | 10 | 1.25 | 12.38 |
| 10 µM beacon | 100 | 1.25 | 12.38 |
| 500 U/µl T7 ligase | 3000 U/µl | 1 | Respectively |
| 10 U/µ Phi 29 polymerase | 10 | 5 | Respectively |
| 0.1 U/µl Pyrophosphatase | 0.1 | 1.25 | Respectively |
| BstZ17I-HF enzyme | 20 | 1 | Respectively |
| 10x NEB buffer | 10 | 5 | 49.50 |
| D.W | 0 | 16.75 | 165.83 |
| TOTAL | | 50 | |

1.3. Determination of Whether Restriction Enzyme Operated on the RCA Amplicon The cleavable DNA (SEQ ID NO: 5) was introduced into the RCA amplicon produced in Example 1.2. The reaction was allowed to proceed and electrophoresis was performed. The 5'-CAG//CTG-3' sequence of the RCA amplicon was recognized and cut by a restriction enzyme.

As a result, the DNA was cut into fragments by the restriction enzyme, as shown in FIG. 6.

Example 2. Confirmation of Efficacy of the RCA-Based Method for Detecting Target Nucleic Acid (Double Cutting)

2.1. Construction of Template, Primer and Cleavable DNA 50 bases around the E545K point mutation of the PIK3CA gene were selected as a target gene and a template, a primer, and a beacon for amplicon detection were constructed, as shown in Table 4, to determine whether the E545K point mutation could be detected by the inventive method.

TABLE 4

Nucleic acid sequences generated in Example 2

| SEQ ID NO. | Name | Sequence |
|---|---|---|
| 6 | Template | 5'-AGT GAT TTC A(1) CCCCC(2) AT GTA GTA GTA TCG ACG TCC C(3) CCCCC(4) GTA TAC(5) CCCCC(6) GTT TCC TCA TAT CCA GTT TC(7) CCCCC(8) GTA TAC(9) CCCCC(10) T CTC CTG CTT(11)-3' |
| 2 | Wild type | 5'-CGA GAT CCT CTC TCT GAA ATC ACT GAG CAG GAG AAA GAT TTT CTA TGG AG-3' |
| 3 | Mutant | 5'-CGA GAT CCT CTC TCT GAA ATC ACT AAG CAG GAG AAA GAT TTT CTA TGG AG-3' |

TABLE 4-continued

Nucleic acid sequences generated in Example 2

| SEQ ID NO. | Name | Sequence |
|---|---|---|
| 7 | Primer | 5'-G GGA CGT CGA TAC TAC TAC AT-3' |
| 8 | Cleavable DNA | 5'-CCC GTA TAC CCC GGG-dabcy1-3' |

The sequence of the template is as follows.

5' phosphate-(1): First target binding region in which the first base T complementarily binds to the base A shown in bold in the sequence (SEQ ID NO: 3) of the mutant.
- (1)-(2): Spacer
- (2)-(3): Primer binding region
- (3)-(4): Spacer
- (4)-(5): Restriction enzyme recognition region
- (5)-(6): Spacer
- (6)-(7): Barcode generation region
- (7)-(8): Spacer
- (8)-(9): Restriction enzyme recognition region
- (9)-(10): Spacer
- (10)-(11): Second target binding region 2.2. Determination of Whether Restriction Enzyme Operated on RCA Amplicon The target nucleic acid having the sequence set forth in SEQ ID NO: 2 or 3 and the primer having the sequence set forth in SEQ ID NO: 7 were introduced into the template (SEQ ID NO: 6) constructed in Example 2.1. Then, RCA was performed using the components in the amounts shown in Table 5. The cleavable DNA (SEQ ID NO: 8) was introduced into the RCA amplicon. The reaction was allowed to proceed and electrophoresis was performed. The 5'-CAG//CTG-3' sequence of the RCA amplicon was recognized and cut by a restriction enzyme.

As a result, the DNA was cut into fragments by the restriction enzyme, as shown in FIG. 7.

TABLE 5

| Component | Initial Concentration | | Volume [μL] |
|---|---|---|---|
| Template_E545K | 5 | μM | 2.5 |
| Starting primer | 10 | μM | 1.25 |
| Molecular Beacon (opt.) | 10 | μM | 0 |
| Bstz17i_Oligo | 100 | μM | 5 |
| Target DNA (diff. conc.) | 100 | μM | 1.25 |
| Phi 29 polymerase buffer | 10 | X | 5 |
| CutSmart buffer | 10 | X | 5 |
| DTT | 100 | mM | 1.25 |
| dNTP | 25 | mM | 5 |
| ATP | 50 | mM | 1.25 |
| BSA in PBS | 10 | mg/mL | 1 |
| Pyrophosphatase | 0.1 | U/μL | 1.25 |
| SplintR ligase | 2.5 | U/μL | 1 |
| Phi 29 polymerase | 10 | U/μL | 5 |
| Bstz17i | 20 | U/μL | 4 |
| D.W | 0 | | 10.25 |
| TOTAL Vol. | | | 50 |

2.3. Identification of the Barcoded Amplicons Using SPR Sensor

A validation experiment was conducted using an SPR sensor to verify the function of the RCA amplicons produced using the template constructed in Example 2.1 as barcodes. The results are shown in FIG. 8. Specifically, the red boxed area shown at the top left of FIG. 8 is estimated as the barcoded DNA. The RCA amplicons were analyzed using an SPR sensor. The bottom of FIG. 8 shows the principle of how the barcodes are distinguished. The RCA amplicons were defined as first barcodes (#1 Encoded DNA). A probe linker (#1 Encoded DNA linker) complementary to the first barcodes and a probe linker (#2 Encoded DNA linker) non-complementary to the first barcodes were previously immobilized on the surfaces of two different analysis channels of the SPR sensor, and thereafter, the RCA amplicons were introduced into the two analysis channels. The resulting SPR detection signals were compared.

As a result, strong detection signals were generated from the channel on which the probe linker complementary to the RCA amplicons was immobilized whereas no detection signal was observed from the channel on which the probe linker non-complementary to the RCA amplicons was immobilized, as shown in the graph at the top right of FIG. 8. These results demonstrate that the amplicons were well produced by RCA according to the inventive method.

Although the particulars of the present disclosure have been described in detail, it will be obvious to those skilled in the art that such particulars are merely preferred embodiments and are not intended to limit the scope of the present invention. Therefore, the true scope of the present invention is defined by the appended claims and their equivalents.

INDUSTRIAL APPLICABILITY

The method for detecting a target nucleic acid and the composition for RCA for carrying out the method according to the present invention can be used to detect mutations at a base level with high sensitivity, and therefore, they are suitable for use in the field of molecular diagnostics.

The invention claimed is:

1. A method for detecting a target nucleic acid based on rolling circle amplification (RCA), comprising:
 (a) preparing a single-stranded nucleic acid from a sample;
 (b) binding a linear template comprising:
  i) target nucleic acid binding regions arranged at both ends to complementarily bind to a target nucleic acid sequence;
  ii) a primer binding region;
  iii) a restriction enzyme binding region; and
  iv) a barcode generation region to the single-stranded nucleic acid, followed by ligation to form a circular template-target nucleic acid complex;
 (c) performing rolling circle amplification in the presence of a primer binding to the primer binding region and a cleavable nucleic acid having the same sequence as that of the restriction enzyme binding region to produce a single-stranded amplicon and treating the single-stranded amplicon with a restriction enzyme such that regions where the single-stranded amplicon complementarily binds to the cleavable nucleic acid are cut to obtain first amplicons comprising barcodes having a sequence complementary to the barcode generation region and separated from the single-stranded amplicon and second amplicons comprising the target nucleic acid sequence; and
 (d) detecting the barcodes of the first amplicons separated from the single-stranded amplicon to determine whether or not the target nucleic acid sequence is present, wherein the circular template-target nucleic acid complex is formed and the barcodes are generated when the target nucleic acid sequence is present in the single-stranded nucleic acid,
 wherein the barcodes of the first amplicons separated from the single-stranded amplicon are detected using a surface measurement sensor comprising a probe complementary to the barcodes.

2. The method according to claim 1, wherein the barcodes have a predefined sequence depending on the target nucleic acid and do not complementarily bind to the target nucleic acid.

3. The method according to claim 1, wherein each of the second amplicons is provided as a single-stranded nucleic acid in step (a).

4. The method according to claim 1, wherein the target nucleic acid is present in plurality.

5. The method according to claim 4, wherein barcode generation regions of different templates corresponding to the target nucleic acids are amplified to generate barcodes and the target nucleic acids are detected using the barcodes.

6. The method according to claim 1, wherein the target nucleic acid binding regions of the template are designed such that a point of interest of the target nucleic acid is ligated to the template by a ligase.

7. The method according to claim 1, wherein, in step (a), the single-stranded nucleic acid is prepared by asymmetric polymerase chain reaction (PCR).

8. The method according to claim 1, wherein, in step (a), the single-stranded nucleic acid is prepared by denaturing double-stranded deoxyribonucleic acid (DNA) extracted from a sample and complementarily binding a blocker DNA to only one single strand of the denatured double-stranded deoxyribonucleic acid.

9. The method according to claim 1, wherein the surface measurement sensor operates based on a method selected from the group consisting of fluorescence, surface plasmon resonance (SPR), quartz crystal microbalance (QCM), and cantilevers.

10. The method according to claim 1, wherein the probe complementary to the barcodes is selected from the group consisting of oligonucleotides, locked nucleic acids (LNAs), peptide nucleic acids (PNAs), and mixtures thereof.

11. The method according to claim 1, wherein when the surface measurement sensor operates based on fluorescence, and wherein a reporter and a quencher are linked to both ends of the probe complementary to the barcodes.

12. The method according to claim 11, wherein the reporter is at least one fluorescent material selected from the group consisting of fluorescein, fluorescein chlorotriazinyl, rhodamine green, rhodamine red, tetramethylrhodamine, FITC, Oregon green, Alexa Fluor, FAM, JOE, ROX, HEX, Texas Red, TET, TRITC, TAMRA, cyanine-based dyes, and thiadicarbocyanine dyes.

13. The method according to claim 11, wherein the quencher is selected from the group consisting of Dabcyl, TAMRA, Eclipse, DDQ,QSY, Blackberry Quencher, Black Hole Quencher, Qxl, Iowa black FQ, Iowa black RQ, IRDye QC-1, and mixtures thereof.

14. The method according to claim 1, wherein the template further comprises a spacer region and a fluorescent probe binding region.

15. The method according to claim 1, wherein the restriction enzyme binding region of the template is present in plurality.

16. The method according to claim 1, wherein the cleavable nucleic acid further comprises sequences at the 5' and 3' ends thereof which do not bind to the template.

17. The method according to claim 1, wherein the cleavable nucleic acid further comprises functional groups or bases at the 5' and 3' ends thereof which inhibit nucleic acid polymerization.

18. The method according to claim 17, wherein the functional groups or bases inhibiting nucleic acid polymerization are selected from the group consisting of amine groups, phosphate groups, alkyl groups, alkane-diols, phosphorothioates, biotin, non-nucleotide linkers, C3-18 spacers, dideoxynucleotide triphosphates (ddNTPs), inverted deoxynucleotide triphosphates (inverted dNTPs), inverted dideoxynucleotide triphosphates (inverted ddNTP), and mixtures thereof.

* * * * *